(12) United States Patent
Liu et al.

(10) Patent No.: US 8,421,635 B2
(45) Date of Patent: Apr. 16, 2013

(54) PATIENT BED

(76) Inventors: Wei-Ting Liu, Hacienda Heights, CA (US); Wei-Hua Lu, Taipei (TW); Chih-Kuei Hu, Jubei (TW)

( * ) Notice: Subject to any disclaimer, the term of this patent is extended or adjusted under 35 U.S.C. 154(b) by 534 days.

(21) Appl. No.: 12/634,694

(22) Filed: Dec. 10, 2009

(65) Prior Publication Data

US 2011/0140869 A1 Jun. 16, 2011

(51) Int. Cl.
*G08B 23/00* (2006.01)

(52) U.S. Cl.
USPC ............... 340/573.1; 340/573.4; 340/286.07; 340/525; 340/664; 340/665; 340/666; 340/667; 340/686.1; 340/3.7; 340/7.1; 5/616; 5/618; 5/624; 5/706; 5/710

(58) Field of Classification Search ............... 340/573.1, 340/573.4, 286.07, 525, 664–667, 686.1, 340/3.7, 7.1; 5/616, 618, 624, 706, 710
See application file for complete search history.

(56) References Cited

U.S. PATENT DOCUMENTS

| 5,335,313 | A * | 8/1994 | Douglas | 704/275 |
| 6,560,798 | B2 * | 5/2003 | Welling et al. | 5/503.1 |
| 6,658,680 | B2 * | 12/2003 | Osborne et al. | 5/600 |
| 6,781,517 | B2 * | 8/2004 | Moster et al. | 340/4.11 |
| 6,829,796 | B2 * | 12/2004 | Salvatini et al. | 5/713 |
| 7,986,242 | B2 * | 7/2011 | Dixon et al. | 340/573.1 |

* cited by examiner

*Primary Examiner* — Tai T Nguyen

(57) ABSTRACT

A patient bed with a multimedia system is disclosed. A patient can access a net work through the multimedia system, and to join a net meeting to chat with other patients. The multimedia system can also provide a consolidated platform of medical information for a doctor or a nurse. An input device of the patient bed may have a touch pad, which allows the patient to control the position of patient support through finger gesture.

12 Claims, 5 Drawing Sheets

PATIENT BED

BACKGROUND OF THE INVENTION

1. Field of the Invention

The present invention relates to a patient bed and its peripheral apparatus for facilitating patient's life during hospital time, and more particularly, for providing the patient to join a net meeting or chat room and more easily to control the patient support of the patient bed.

2. Description of the Prior Art

A patient bed is an essential equipment in hospital. Traditionally, patient bed is placed in a ward with some life monitoring devices around it. A doctor has to bring patients' medical records when he is visiting his patients. Sometimes, some patients' situation is complicated, and hand-bring medical records are hard to explain the situation to patients or hard for doctor to record every detail in medical records.

A patient with chronic disease need to stay on a patient bed for a long period. Right now, the only entertainment for a patient is a hanging television in his ward, and sometimes this is only for a higher price ward. Besides, modern people are much busier to accompany their relatives who stay at hospital. Therefore, the patients with chronic disease will lack human interaction and stay in boring life on patient beds. Since there are medical information requirement and an entertainment need for patients, there is a large room for improvement of patient bed.

SUMMARY OF THE INVENTION

It is therefore a primary objective of the claimed invention to provide a patient bed with a multimedia system.

The present invention discloses a patient bed comprising a patient support; a multimedia system, for communicating with an external electronic device to receive medical information or multimedia information, the multimedia system comprises a panel, capable of displaying medical information and multimedia information; an input device, for allowing a user to input a command to the multimedia system; a microphone, for allowing the user to speak via the microphone; and a speaker; wherein the multimedia system is capable of controlling the patient support.

The present invention also discloses a patient bed comprising a touch panel, for allowing a user to input a command, wherein the command is a gesture of at least one finger; a patient support comprising a motor, for adjusting a position of the patient support relative to a floor; and a motor control system, coupled to the patient support, for controlling the motor to further control the position according to the command.

The present invention further discloses a patient bed comprising a patient support; a multimedia system, for communicating with an external electronic device to receive medical information or multimedia information, the multimedia system comprises a panel, capable of displaying medical information and multimedia information; an input device, for allowing a user to input a command to the multimedia system; a microphone, for allowing the user to speak via the microphone; and a speaker; and an emergency button, for emitting an emergency signal when the emergency button is pressed.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
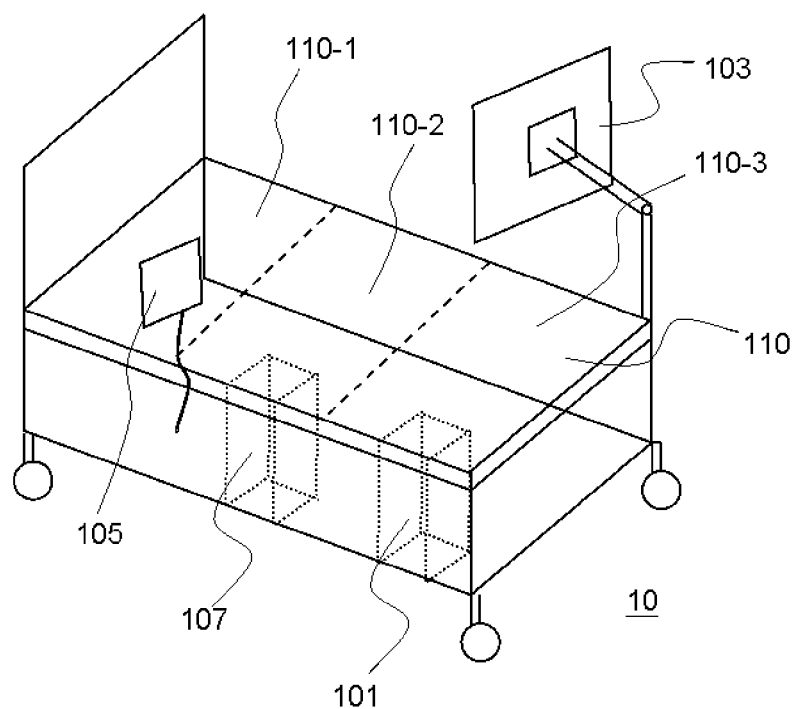
FIG. 1 is a schematic diagram of a patient bed according to an embodiment of the present invention.

Please refer to FIG. 1, which is a schematic diagram of a patient bed 10 according to an embodiment of the present invention. The patient bed 10 comprises a multimedia system 101, an output device 103, an input device 105, a patient support 110 and a motor control system 107. The patient support 110 can be divided into several portions according to different patient bed design. For example, as shown in FIG. 1, the patient support 110 is divided into three portions, the head portion 110-1, the middle portion 110-2 and the leg portion 110-3. The patient support 110 can also divided into more than three portions for better support, or only divided into two portions, all of these are not escape from the scope of this invention.

Figure 2:
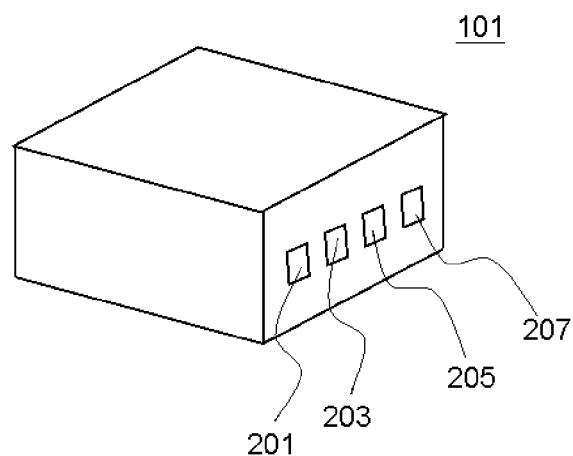
FIG. 2 is a multimedia system of a patient bed shown in FIG. 1.

The multimedia system 101 can be placed under the patient support 110 as shown in FIG. 1, or be placed nearby the patient bed 10. The detail of the multimedia system 101 is shown in FIG. 2. The multimedia system 101 has a network port 201, a signal input port 203, a signal out port 205 and a control port 207. The network port 201 can be a RJ-45 port, a RJ-15 port, a RJ-11 port, a RJ-14 port, a BNC port or other network port. The network port 201 can also be an antenna for receiving or transferring information of wireless network, such as Wi-Fi (IEEE 802.11), Wi-Max (IEEE 802.16) etc. The signal input port 203 is coupled to the input device 105, for receiving the input command or input signal from a user. The signal out port 205 is coupled to the output device 103, for outputting video information or audio information to the output device 103. The control port 207 is coupled to a motor control system 107 for controlling the patient support 110 position relative to the floor.

Figure 3:
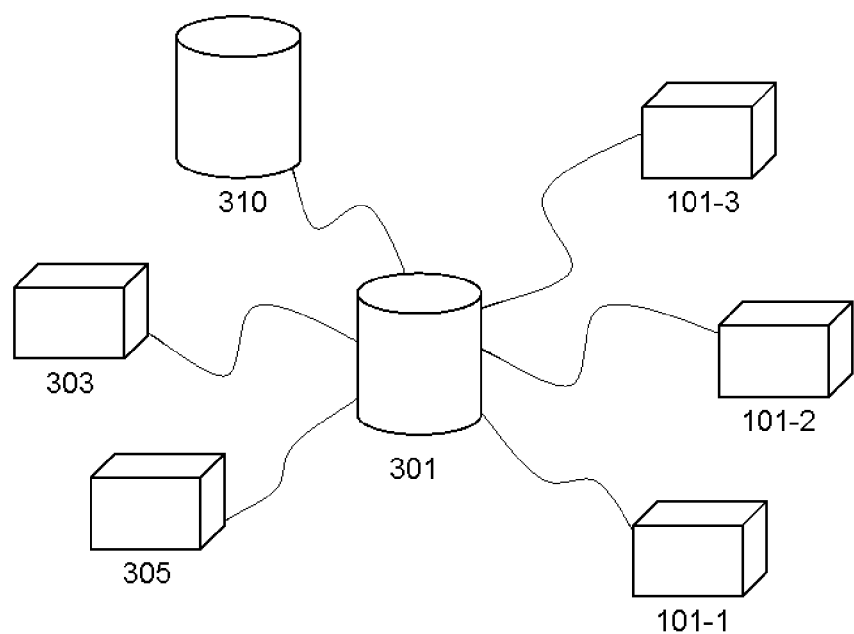
FIG. 3 is a schematic diagram of the network system according to an embodiment of the present invention.

The multimedia system 101 can access network through the network port 201, and the network could be intranet or internet. Please refer to FIG. 3, the patient at multimedia system 101-1 site can access the server 301 through an intranet system. Other patients at multimedia system 101-2 site and multimedia system 101-3 site can also access the server 301. Every patient who accesses the server 301 can start a net meeting or a chat room, other patients who want to join the net meeting or the chat room can join it directly or ask permission to the host. The net meeting or the chat room will show other patients' photo on the output device 103, which can be a monitor. Each of them can talk to other patients through the network system, and see their faces at the same time. The host of the net meeting or the chat room can set black list to block someone if the host doesn't want a specific patient to join the net meeting or the chat room.

The patient at multimedia system 101 site can also access the network system to browse the net through either internet or intranet, read the news, read some articles or watch video. A doctor can use the multimedia system 101 to access the server 301 and retrieve the patient's medical record. By this way, doctor can have more detail information of the patient;

include X-ray photos, MRI photos or what medicine the patient has taken. A nurse can also use the multimedia system 101 to input the patient's information, such as the patient's body temperature, pulse, weight, what medicine has been taken, what food has been eaten or other information. The multimedia system can consolidate all medical information of the patient so the doctor or the nurse can easily understand the comprehensive condition of the patient.

Figure 4:
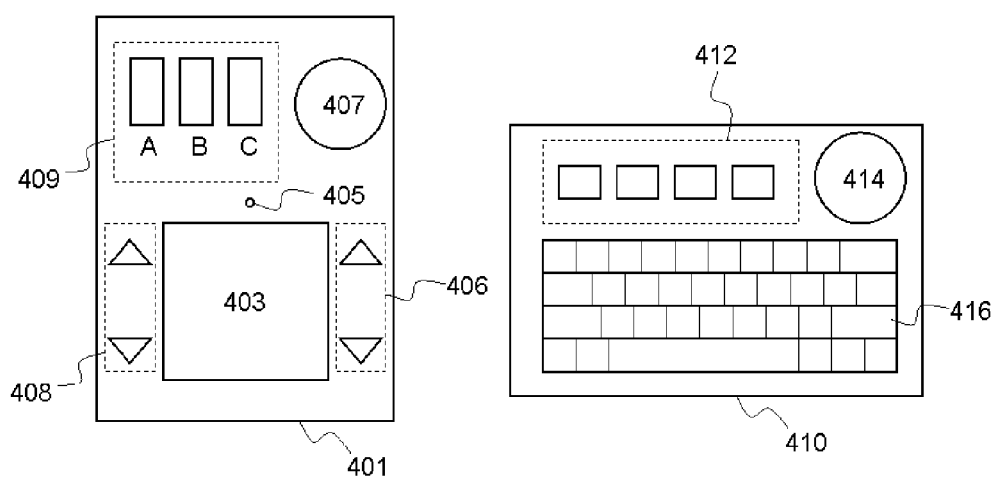
FIG. 4 is a schematic diagram of an input device according to an embodiment of the present invention.
Figure 5:
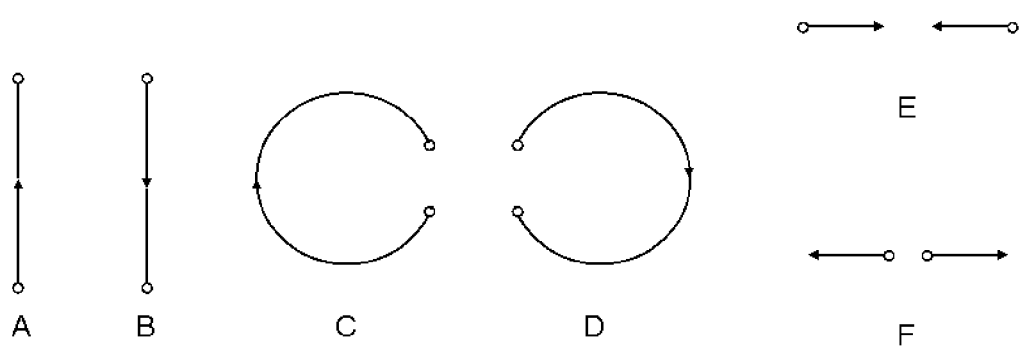
FIG. 5 is a schematic diagram of finger gesture according to an embodiment of the present invention.

The input device 105 can be placed nearby the patient's side. The input device 105 can be a keyboard, a touch pad a mouse or some control buttons. The patient can easily join a net meeting or chat room through the input device 105. Please refer to FIG. 4, which illustrates two types of the input device 105. The input device 401 comprises a touch pad 403, some function buttons 409, microphone 405, channel selection 408, volume selection 406 and an emergency button 407. The function buttons 409 may have some specific functions, such as button A is joining or quitting a net meeting, button B is watching TV and button C is browsing web. The function buttons 409 can have more or less buttons, and be assigned to different functions, such as raise the patient support 110 or flat the patient support 110. The patient can use the touch pad 403 to control a cursor on the output device 103, or use predefined gesture of finger to input command to the multimedia system 101. Some predefined gestures are shown in FIG. 5, which can be one-click, double clicks, upward movement (A), downward movement (B), clockwise circle (C), counterclockwise circle (D), two fingers moving inward (E) and two fingers moving outward (F). Each predefined gesture is corresponding to a predefined command. For example, the patient can use upward movement to raise the patient support 101 or to turn up the volume, downward movement to lower the patient support 101 or turn down the volume, clockwise circle or two fingers moving inward to fully raise the patient support 101 or change to next mode, counterclockwise circle or two fingers moving outward to fully lower the patient support 101 or change back to previous mode. The input device 410 is another example of the input device 105, which comprises a keyboard region 416, function buttons 412 and an emergency button 414. The patient can use the keyboard to input command to the multimedia system 101, or use the function buttons 412 to input special command. Both input device 401 and input device 410 has an emergency button. The patient can use the emergency button whenever he/she not feel good, or when the patient see the other patient on the net meeting has some physical problem and unable to press the emergency button by himself/herself. The microphone 405 can receive the voice of the patient, and send the voice signal to the multimedia system 101. The multimedia system 101 will send out the voice signal to another patient when the system is in net meeting mode, and the multimedia system 101 will recognize the voice when the system is in voice control mode.

The motor control system 107 has a motor to adjust the patient support 110 according to a command receiving from the input device 105. The command of the input device 105 can be sent to the motor control system 107 directly, or be sent to the multimedia system 101 first then the multimedia system 101 controls the motor control system 107.

To sum up, the present invention provides the patient a more enjoyment moment during hospital time, especially provides the patient to chat with other patients even each of them are in different wards. So the patient will not be limited by the equipments and will not suffer affection by other patients' germ or virus. The doctor and nurse and also use the multimedia system to consolidate all patients' medical information, so the real and complete condition of the patients can be under control.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A patient bed comprising:
   a patient support; and
   a multimedia system, for communicating with an external electronic device to receive medical information and multimedia information, the multimedia system comprises:
   a panel, configured to display medical information and multimedia information;
   an input device, for allowing a user to input a command to the multimedia system;
   a microphone, for allowing the user to speak via the microphone; and
   a speaker;
   wherein the multimedia system is capable of controlling the patient support.

2. The patient bed of claim 1, wherein the multimedia information comprises net meeting information.

3. The patient bed of claim 2, wherein the multimedia system further comprises: a controller, for executing a net meeting program to perform a net meeting function between the multimedia system and the external device.

4. The patient bed of claim 1, wherein the input device comprising a touch pad.

5. The patient bed of claim 4, wherein the touch pad receives the command from the user such that the multimedia system control a position of the patient support according to the command.

6. The patient bed of claim 1, wherein the multimedia system communicates with an external electronic device via an internet or an intranet.

7. A patient bed comprising:
   a patient support; and
   a multimedia system, for communicating with an external electronic device to receive medical information and multimedia information, the multimedia system comprises:
   a panel, configured to display medical information and multimedia information;
   an input device, for allowing a user to input a command to the multimedia system;
   a microphone, for allowing the user to speak via the microphone;
   a speaker; and
   an emergency button, for emitting an emergency signal when the emergency button is pressed.

8. The patient bed of claim 7, wherein the multimedia information comprises net meeting information.

9. The patient bed of claim 8, wherein the multimedia system further comprises: a controller, for executing a net meeting program to perform a net meeting function between the multimedia system and the external device.

10. The patient bed of claim 7, wherein the input device comprising a touch pad.

11. The patient bed of claim 10, wherein the touch pad receives the command from the user such that the multimedia system control a position of the patient support according to the command.

12. The patient bed of claim 7, wherein the multimedia system communicates with an external electronic device via an internet or an intranet.

\* \* \* \* \*